United States Patent
Righetti

(10) Patent No.: US 6,605,068 B2
(45) Date of Patent: Aug. 12, 2003

(54) GRAVITY DRAINAGE CORD

(75) Inventor: Roberto Righetti, Via S. Benedetto, 1469-40018 S. Pietro In Casale (IT)

(73) Assignees: Med Europe S.r.l., S. Pietro In Casale (IT); Roberto Righetti, S. Pietro In Casale (IT)

( * ) Notice: Subject to any disclaimer, the term of this patent is extended or adjusted under 35 U.S.C. 154(b) by 34 days.

(21) Appl. No.: 09/752,531

(22) Filed: Jan. 3, 2001

(65) Prior Publication Data

US 2001/0005784 A1 Jun. 28, 2001

(51) Int. Cl.⁷ ............................................. A61M 27/00
(52) U.S. Cl. ....................................... 604/264
(58) Field of Search ......................... 604/264

(56) References Cited

U.S. PATENT DOCUMENTS

| | | | |
|---|---|---|---|
| 3,753,439 A | * 8/1973 | Brugarolas et al. | 604/43 |
| 3,823,720 A | * 7/1974 | Tribble | 604/43 |
| 4,553,966 A | 11/1985 | Korteweg | |
| 5,053,021 A | 10/1991 | Feibus | |
| 5,171,307 A | 12/1992 | Sanning | |
| 5,180,375 A | * 1/1993 | Feibus | 604/204 |
| 5,358,492 A | * 10/1994 | Feibus | 604/264 |
| 5,549,585 A | * 8/1996 | Maher et al. | 604/317 |
| 5,683,778 A | * 11/1997 | Crosier | 428/59 |
| 5,876,400 A | * 3/1999 | Songer | 606/45 |

* cited by examiner

Primary Examiner—Paul J. Hirsch
(74) Attorney, Agent, or Firm—Guido Modiano; Albert Josif; Daniel O'Byrne

(57) ABSTRACT

A gravity drainage cord formed by braiding a plurality of strands of silk of the type used for surgical sutures, and fitted loosely, in the median region, in a tubular sheath made of a material such as silicone which is adapted to facilitate sliding with respect to tissue, increases biocompatibility and allows optional coupling to mechanical aspiration units.

13 Claims, 1 Drawing Sheet

GRAVITY DRAINAGE CORD

BACKGROUND OF THE INVENTION

The present invention relates to a gravity drainage cord.

When draining wounds, the most recent drainage tubes, which entail the presence of low- or high-vacuum mechanical aspiration units, tend to clog due to the presence of clots of blood or other organic substances: accordingly, it is necessary to periodically use devices known as tube squeezers, which cause discomfort and suffering to patients.

It is also known to drain wounds by using a simple cotton gauze which protrudes slightly from the wound and conveys outside the liquid components, allowing faster cicatrization: this system derives from a method used since the days of the ancient Egyptians.

However, the use of cords of rolled-up gauze causes severe pain to the patient during extraction from the wound, since the gauze tends to bond with the walls of the wound.

Additionally, since the material that constitutes the gauze is not very strong, fragments of particles often break off and contaminate the wound, especially during the extraction of the drainage.

SUMMARY OF THE INVENTION

The aim of the present invention is to obviate the cited drawbacks of conventional devices, i.e., to devise a gravity drainage cord which does not leave residues in the wound even during extraction, does not clog up in the presence of organic residues or clots and does not cause pain to the patient during extraction, since it is completely free and does not bond to the walls of the wound.

Within the scope of this aim, an object of the present invention is to provide a structure which is simple, relatively easy to provide in practice, safe in use, effective in operation and relatively low in cost.

These and other objects are achieved by the present gravity drainage cord, characterized in that it is formed by braiding a plurality of strands of silk of the type used for surgical sutures, and in that in the median region it is fitted loosely in a tubular sheath made of a material such as silicone which is adapted to facilitate sliding with respect to tissues, increases biocompatibility and allows optional coupling to mechanical aspiration units.

BRIEF DESCRIPTION OF THE DRAWINGS

Further characteristics and advantages will become better apparent from the following detailed description of a preferred but not exclusive embodiment of a gravity drainage cord according to the invention, illustrated only by way of non-limitative example in the accompanying drawings, wherein.

DESCRIPTION OF THE PREFERRED EMBODIMENTS

Figure 1:
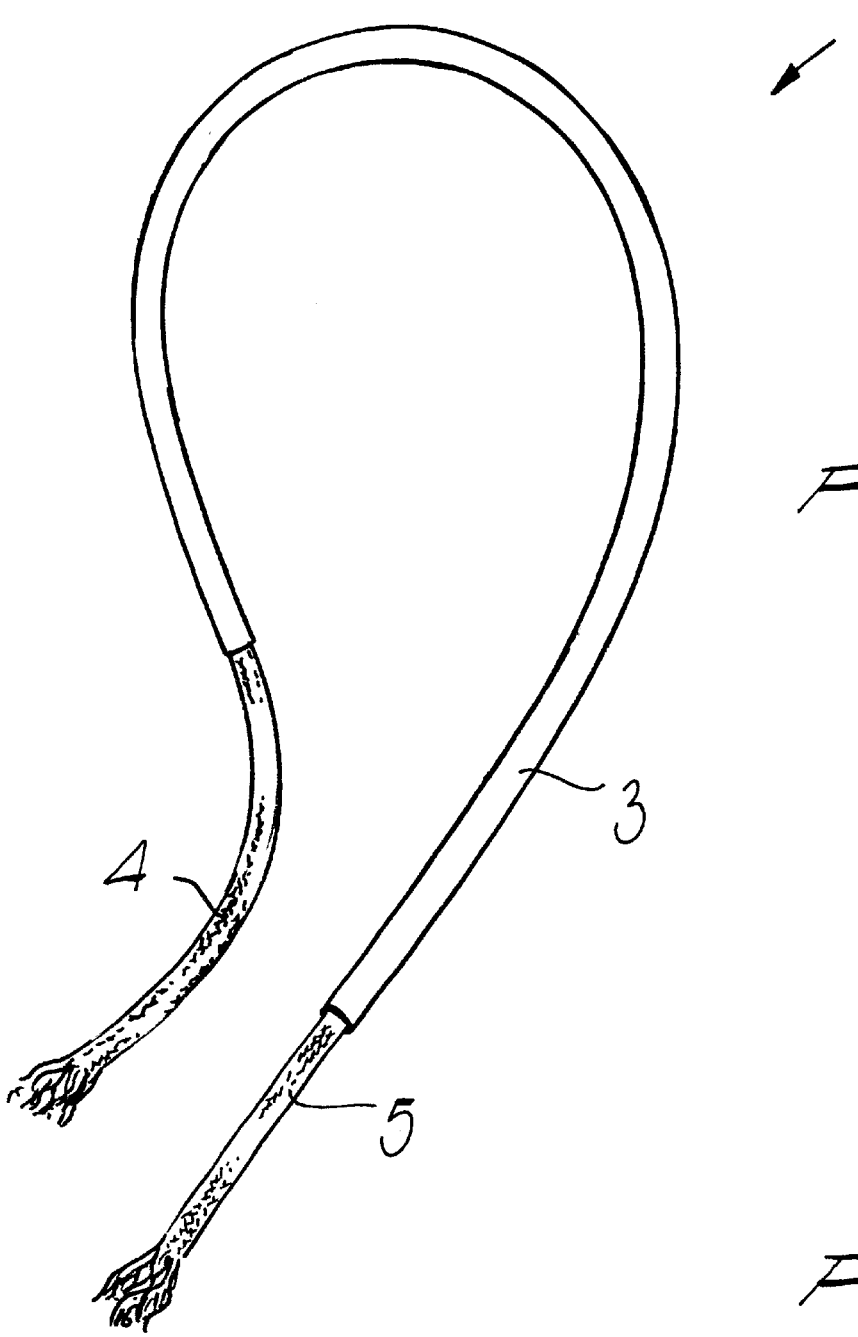
FIG. 1 is a perspective view of a gravity drainage cord according to the invention.
Figure 2:
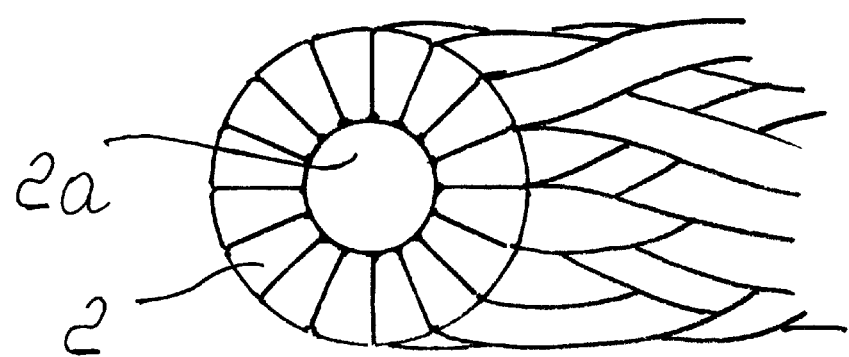
FIG. 2 is a schematic view of a segment of cord.

With reference to the above figures, 1 generally designates the gravity drainage cord according to the invention.

The cord 1 is formed by braiding (of the kind used to form shoelaces) a plurality of strands 2 of silk of the type used for surgical sutures: advantageously, the strands 2 of the cord are eight, twelve, sixteen in number, are twisted and wound around a central core 2a, which is in turn constituted by twisted filaments.

It is noted that the silk strands used for sutures are treated with waxy substances to prevent their impregnation with organic liquids, whereas in the invention the silk is instead not treated, so as to increase the effect of drainage and removal of organic liquids by capillary action.

In the middle region, the cord 1 is inserted loosely in a tubular sheath 3 made of a material such as plastics, particularly silicone for medical uses, which has been extensively tested in the medical field.

The sheath 3 facilitates sliding with respect to tissues during removal of the cord, increases biocompatibility and allows optional coupling to mechanical aspiration units.

The end portions 4 and 5 of the cord that protrude from the sheath 3 facilitate the removal of liquids from the wound and also allow small movements of the silk with respect to the sheath in order to remove any clots or obstacles preventing the correct flow of the liquids without causing pain to the patient.

According to requirements, the sheath can have a radioopaque band for identification.

It is noted that it is possible to insert a plurality of cords (two, three or more) in a single sheath 3; in this case it is possible to open out the cords and distribute them, spread out, within the wound in order to increase the drainage effect.

The portion of tubular sheath 3 designed to be inserted in the cavity to be drained can be affected by a plurality of radial holes which facilitate drainage.

After a first period lasting a few days, the silk cord is removed by sliding it out: in this case, the opening of the tubular sheath can be closed by a removable cap.

It has thus been shown that the invention achieves the intended aim and object and in particular that it leaves no residues in the wound even during extraction, does not clog up in the presence of organic residues or clots, and does not cause pain to the patient during extraction, being completely free and not tending to bond to the walls of the wound.

The invention thus conceived is susceptible of numerous modifications and variations, all of which are within the scope of the inventive concept.

All the details may furthermore be replaced with other technically equivalent elements.

In practice, the materials employed, as well as the shapes and the dimensions, may be any according to requirements without thereby abandoning the scope of the protection of the appended claims.

What is claimed is:

1. A gravity drainage cord, comprising:
    a braiding constituted by a plurality of braided strands of silk of the type used for surgical sutures; a tubular sheath which is fitted loosely over said braiding in a median region of the cord so that end portions thereof protrude from the sheath, said tubular sheath being made of a plastic material for medical use that facilitates sliding with respect to tissues and increases biocompatibility of the drainage cord.

2. The cord of claim 1, wherein said strands are made of a silk material with capillary action for increased drainage effect.

3. The cord of claim 1, constituted by a plurality of cords constituted by braided strands of silk inserted in a said tubular sheath, the cords having the end portions protruding from said tubular sheath and adapted for being spread open inside a wound for increased drainage effect.

4. The cord of claim 1, comprising a central core constituted by twisted filaments, said plurality of silk strands forming said braiding being braided around said core.

5. The cord of claim 4, wherein said braiding is formed by eight strands twisted and wound around said core.

6. The cord of claim 4, wherein said braiding is formed by twelve strands twisted and wound around said core.

7. The cord of claim 4, wherein said braiding is formed by sixteen strands twisted and wound around said core.

8. The cord of claim 1, further comprising a portion to be inserted in a cavity to be drained, said portion being provided with a plurality of radial holes for facilitating drainage.

9. The cord of claim 1, provided with a removable cap for closing an opening of the tubular sheath upon post-surgery extraction of the cord from the sheath.

10. A gravity drainage cord, comprising:

a braiding constituted by a plurality of braided strands of silk of the type used for surgical sutures;

a tubular sheath which is fitted loosely over said braiding in a median region of the cord so that end portions thereof protrude from the sheath, said tubular sheath being made of silicone for medical use that facilitates sliding with respect to tissues and increases biocompatibility of the drainage cord.

11. A gravity drainage cord, comprising:

a central core constituted by twisted filaments;

a plurality of strands of silk of the type used for surgical sutures which are twisted and wound around said central core so as to form a braiding;

and a tubular sheath which is fitted loosely over said braiding in a median region of the cord so that end portions thereof protrude from the sheath, said tubular sheath being made of a plastic material for medical use that facilitates sliding with respect to tissues and increases biocompatibility of the drainage cord.

12. The cord of claim 11, wherein said filaments that form said central core are made of silk.

13. The cord of claim 11, wherein said tubular sheath is made of silicone.

* * * * *